United States Patent [19]

Warriner

[11] Patent Number: Plant 6,091

[45] Date of Patent: Feb. 2, 1988

[54] ROSE PLANT JACIAT

[75] Inventor: William A. Warriner, Tustin, Calif.

[73] Assignee: Jackson & Perkins Company, Medford, Oreg.

[21] Appl. No.: 825,740

[22] Filed: Feb. 3, 1986

[51] Int. Cl.[4] ..... A01H 5/00

[52] U.S. Cl. ..... Plt./10

[58] Field of Search ..... Plt. 10

*Primary Examiner*—Robert E. Bagwill

*Attorney, Agent, or Firm*—Manford R. Haxton

[57] ABSTRACT

A miniature rose variety having vigorous, compact growth habit, bright red flowers, excellent mildew resistance, attractive glossy green foliage and long stipules for such small leaves.

1 Drawing Figure

This present invention relates to a new and distinct variety of rose plant of the miniature class which was originated by crossing an unnamed variety with the variety, Funny Girl, U.S. Plant Pat. No. 5,249.

The primary objective of this breeding was to produce a new rose variety of the miniature class exhibiting bright red flowers on a compact dwarf shrub. This objective was substantially achieved along with other desirable improvements as evidenced by the following unique combination of characteristics which are outstanding in the new variety and which distinguish it from its parents as well as from all other varieties of which I am aware:

1. Bright red flower color;
2. Small dark green glossy foliage;
3. Long stipules for such small leaves;
4. Good mildew resistance; and
5. Vigorous growth and constant blooming.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Unnamed variety.

*Pollen parent.*—Funny Girl, U.S. Plant Pat. No. 5,249.

Classification:

*Botanical.*—Rosa hybrid.

*Commercial.*—Miniature.

FLOWER

Observations made from specimens grown in a greenhouse at Irvine, Calif. in September, 1985.

Blooming habit: Continuous.

Bud:

*Size.*—½ to ¾" when petals start to unfurl.

*Form.*—Short, blunt top.

*Color.*—When sepals first divide, a bright red (Red Group 45A); when half blown, upper side of petals Red Group 45A; lower side of petals Red Group 45C.

*Sepals.*—Color: Green Group 138B. Three appendaged sepals normally appendaged. Two unappendaged sepals, hairy edge.

*Receptacle.*—Color: Green, Green Group 143C. Shape: Funnel. Size: Medium. Surface: Smooth and covered with very fine hair.

*Peduncle.*—Length: Short. Surface: Smooth and covered with very fine hairs and occasional glands. Color: Medium green. Strength: Stiff.

Open bloom:

*Size.*—Small. Average open size 2½".

*Borne.*—Single or several together in clusters.

*Stems.*—Short, strong.

*Form.*—When first open, flat. Permanence: Retains its form to the end, outer petals curl back.

*Petalage.*—Number of petals under normal conditions: 25.

*Color.*—Center of flower: Upper side of petals, Red Group 45A; reverse side of petals, Red Group 45C. Base of petals, small white patch. Major color: Red Group 45A.

*Variegations.*—Occasional white streak on outer petals.

*Discoloration.*—General tonality at end of first day: None. Third day: None.

*Fragrance.*—Slight.

Petals:

*Texture.*—Thick.

*Shape.*—Obovate.

*Form.*—Tips slightly recurved with edges slightly quilled.

*Arrangement.*—Imbricated. Petaloids in center, few.

*Persistence.*—Drop off cleanly.

*Lastingness.*—On the plant, long. As cut flower, long.

Reproductive parts:

*Anthers.*—Large. Color: Yellow. Arrangement: Regular around styles.

*Filaments.*—Color: Reddish brown.

*Pollen.*—Gold yellow.

*Styles.*—Color: Reddish.

*Stigmas.*—Color: Greenish white.

PLANT

Form: Bush.
Growth: Vigorous, compact.
Foliage: Number of leaflets on normal mid-stem leaves: 5.
*Size.*—Small.
*Quantity.*—Abundant.
*Color.*—New foliage: Reddish. Old foliage: Bright glossy green.
Leaflets:
*Shape.*—Oval pointed.
*Texture.*—Glossy, smooth.
*Edge.*—Serrated.
*Serration.*—Single.
*Petiole.*—Rachis: Color: Reddish. Underside: Smooth, with prickles.
*Stipules.*—Long, bearded.
*Disease resistance.*—Resistant to mildew, under normal growing conditions at Irvine, Calif.

Wood:
*New wood.*—Color: Reddish. Bark: Smooth.
*Old wood.*—Color: Green. Bark: Smooth.
Prickles:
*Quantity.*—On main canes from base: Ordinary. On laterals from main canes: Ordinary.
*Form.*—Straight to hooked slightly downward.
*Color when young.*—Red.
Small prickles:
*Quantity.*—On main stalks, none. On laterals, none.

I claim:

1. A new and distinct variety of rose plant of the miniature class, substantially as herein shown and described, characterized particularly as to novelty by the unique combination of its vigorous, compact growth habit, bright red flowers, excellent mildew resistance, attractive glossy green foliage and long stipules for such small leaves.

* * * * *

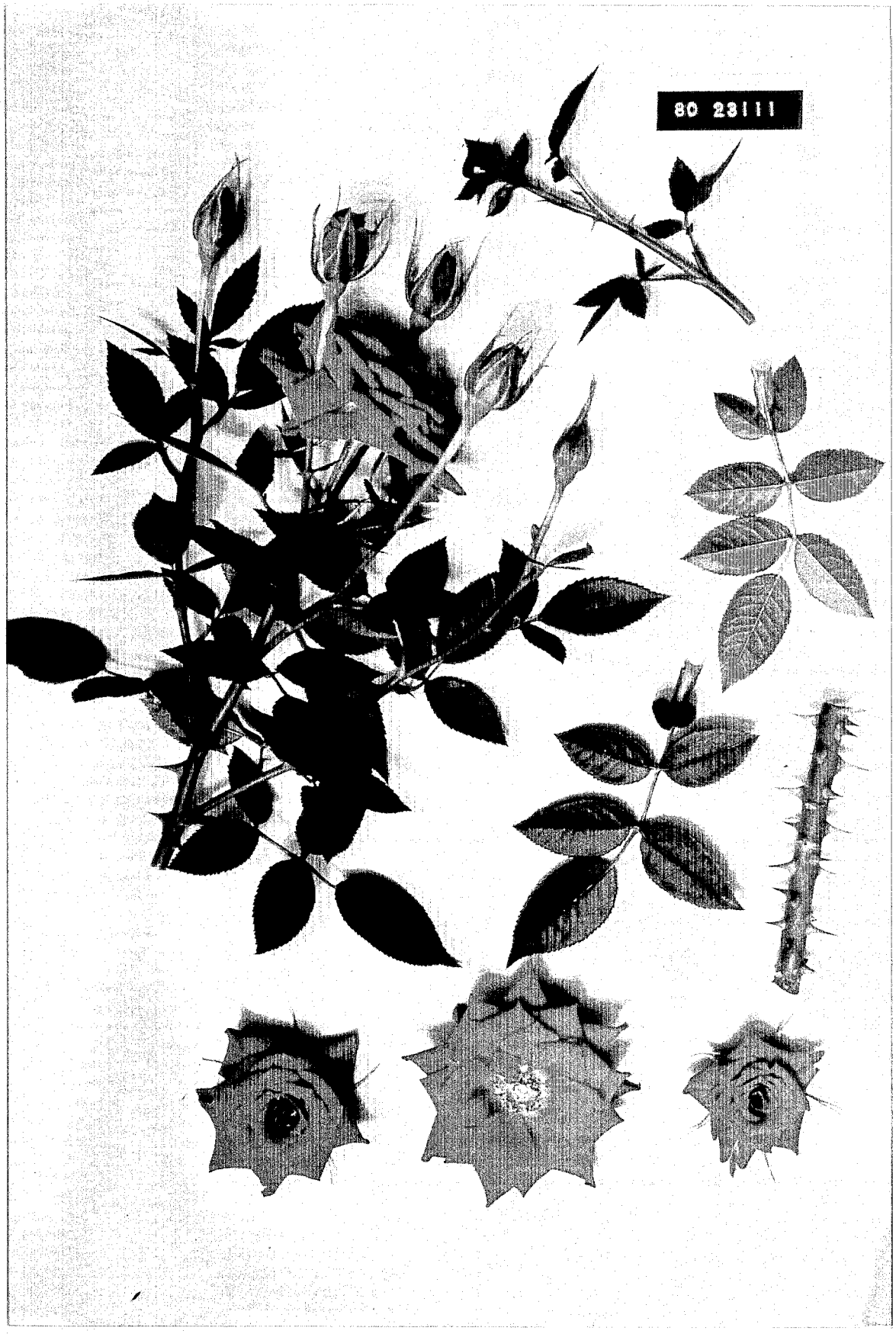
80 23111